(12) United States Patent
Bourdat et al.

(10) Patent No.: US 11,905,550 B2
(45) Date of Patent: Feb. 20, 2024

(54) PROCESS FOR PREPARING A BIOLOGICAL SAMPLE

(71) Applicants: Commissariat a l'energie atomique et aux energies alternatives, Paris (FR); SERVICE DEPARTEMENTAL METROPOLITAIN D'INCENDIE ET DE SECOURS (SDMIS), Lyons (FR)

(72) Inventors: Anne-Gaelle Bourdat, Grenoble (FR); Gregory Wenisch, Lyons (FR)

(73) Assignees: Commissariat a l'energie atomique et aux energies alternatives, Paris (FR); SERVICE DEPARTMENTAL METROPOLITAIN D'INCENDIE ET DE SECOURS (SDMIS), Lyons (FR)

( * ) Notice: Subject to any disclaimer, the term of this patent is extended or adjusted under 35 U.S.C. 154(b) by 1161 days.

(21) Appl. No.: 16/585,729

(22) Filed: Sep. 27, 2019

(65) Prior Publication Data
US 2020/0102597 A1  Apr. 2, 2020

(30) Foreign Application Priority Data
Sep. 28, 2018 (FR) ..................... 18 58926

(51) Int. Cl.
*C12Q 1/68* (2018.01)
*C12Q 1/6806* (2018.01)
(Continued)

(52) U.S. Cl.
CPC ...... *C12Q 1/6806* (2013.01); *B01L 3/502746* (2013.01); *B01L 3/502753* (2013.01);
(Continued)

(58) Field of Classification Search
CPC ............. C12Q 1/6806; B01L 3/502746; B01L 3/502753; B01L 2300/0681;
(Continued)

(56) References Cited

U.S. PATENT DOCUMENTS 7,993,821 B2    8/2011  Chiu et al.
9,314,795 B2 *  4/2016  Selden ................ B01L 3/50273
                        (Continued)

FOREIGN PATENT DOCUMENTS

FR          3 049 061 A1    9/2017

OTHER PUBLICATIONS

Flaender et al. (Sensors and Actuators B, 2018, 258:148-155) (Year: 2018).*
French Preliminary Search Report dated Jun. 3, 2019 in French Application 18 58926, filed on Sep. 28, 2018 (with English Translation of Categories of Cited Documents & Written Opinion).

*Primary Examiner* — Stephanie K Mummert
(74) *Attorney, Agent, or Firm* — Oblon, McClelland, Maier & Neustadt, L.L.P.

(57) ABSTRACT

A process for preparing a biological sample including biological species, implemented in a preparation system, the preparation system including a device that includes: a housing, a first channel provided in the housing, a second channel provided in the housing, a chamber into which the first channel and the second channel open, a filter separating the chamber into two distinct spaces, the process including the following steps: injection of the biological sample in the form of a fluid via the first channel to concentrate biological species in the first space of the chamber of the device, injection of an immunological buffer fluid via the second channel of the device so as to at least partially elute the biological species with the immunological buffer fluid.

14 Claims, 4 Drawing Sheets

(51) Int. Cl.
  *B01L 3/00* (2006.01)
  *C12N 15/10* (2006.01)
  *G01N 1/28* (2006.01)

(52) U.S. Cl.
  CPC ......... *C12N 15/1017* (2013.01); *G01N 1/286* (2013.01); *B01L 2300/0681* (2013.01); *B01L 2400/0403* (2013.01)

(58) Field of Classification Search
  CPC ......... B01L 2200/027; B01L 2300/123; B01L 2400/0622; C12N 15/1017; G01N 1/286; C12M 47/06
  See application file for complete search history.

(56) References Cited

U.S. PATENT DOCUMENTS

| | | |
|---|---|---|
| 10,752,936 B2 * | 8/2020 | Gosselin ................ C12Q 1/686 |
| 2004/0142463 A1 | 7/2004 | Walker et al. |
| 2005/0176135 A1 * | 8/2005 | Jones ................ B01L 3/502738 435/288.5 |
| 2006/0257992 A1 | 11/2006 | McDevitt et al. |
| 2008/0248499 A1 | 10/2008 | Chiu et al. |
| 2010/0279321 A1 | 11/2010 | Chiu et al. |
| 2014/0220673 A1 | 8/2014 | Chiu et al. |
| 2014/0356890 A1 | 12/2014 | Lee et al. |
| 2017/0268041 A1 | 9/2017 | Gosselin et al. |

* cited by examiner

PROCESS FOR PREPARING A BIOLOGICAL SAMPLE

TECHNICAL FIELD OF THE INVENTION

The present invention relates to a process for preparing a biological sample to extract therefrom biological species to be analysed, implemented using a preparation device.

The process is characterized by the fact that it allows, in the same device and according to the steps that are implemented, from the same biological sample comprising biological species (bacteria, viruses, moulds, yeasts, cells, toxins or animal or plant tissues), to prepare several samples containing each of the different biological species of interest (DNA molecules and membrane proteins in particular).

The invention also relates to a preparation system used to implement said process.

STATE OF THE ART

Document US2004/142463A1 (D2) discloses a solution for preparing a sample, particularly a blood sample.

Patent application EP3222989A1 discloses a device for lysing biological species present in a sample, in particular to extract DNA molecules for detection by PCR amplification. On the other hand, for preparing a sample for immunological detection, few truly suitable solutions exist. As a general rule, detection tests are performed directly on the samples, without any concentration or purification steps. This is the case for samples such as urine, swabs, food samples, water, etc. For blood, a filtration or centrifugation step is performed to extract serum or plasma. However, in order to set up an effective immunological reaction, it is essential to:

Know the quantity of targeted biological species;

Control the salinity of the sample;

Control the pH during the process;

Furthermore, the preparation of a sample for immunological detection and the preparation of a sample for DNA extraction are often very different in terms of the protocols used, even though some steps may be common.

There are therefore few processes that allow simple preparation of a sample for immunological detection.

Moreover, there is no process that can be used to prepare, from a single device and a single sample, a first sample for immunological detection and a second sample for amplification reaction.

DISCLOSURE OF THE INVENTION

This aim is achieved by a process for preparing a biological sample comprising biological species, implemented in a preparation system, said preparation system comprising a device that includes:

A housing with at least one opening,

A first channel provided in said housing,

A second channel provided in said housing,

A chamber into which the first channel and the second channel lead,

A filter separating said chamber into two distinct spaces, so as to define a first space into which said first injection channel leads and a second space into which said second channel leads, said filter having a porosity suitable for retaining said biological material to be analysed, Said process comprising the following steps:

Injection of the biological sample in the form of a fluid via the first channel to concentrate biological species in the first space of the chamber of said device, Lysis of said biological species in said chamber to grind said biological species and separate the membranes from the intracellular material, Elution of the intracellular material by injecting an amplification buffer through the first channel of the device, to elute said material via the second channel, Injection of an immunological buffer fluid via the second channel of the device so as to at least partially elute said biological species with said immunological buffer fluid.

According to one feature, the process includes a washing step after concentration, carried out by injecting a wash buffer via said first channel of the device, to purify said biological species.

The invention also relates to a system for preparing a biological sample that comprises biological species, said preparation system comprising a preparation device that includes:

A housing with at least one opening,

A first channel provided in said housing,

A second channel provided in said housing,

A chamber into which the first channel and the second channel lead,

A filter separating said chamber into two distinct spaces, so as to define a first space into which said first injection channel leads and a second space into which said second channel leads, said filter having a porosity suitable for retaining said biological material to be analysed said system comprising a fluid circuit connected to said device, said fluid circuit comprising several controlled valves and a processing and control unit configured to control each valve in order to implement the process as defined above.

According to one feature, the fluid circuit has a first valve arranged to connect a first end of the first channel of the device to an injection channel or to an immunological detection device.

According to another feature, the fluid circuit has a second valve and three tanks, and the second valve is arranged to connect said injection channel to one of said three tanks.

According to another feature, the fluid circuit has a third valve arranged to connect a first end of the second channel to an amplification detection device or to a third channel.

According to another feature, the fluid circuit has a fourth valve arranged to connect the third channel to a tank to contain an immunoassay buffer or to a waste bin.

The invention also relates to the use of the system as defined above, to prepare a biological sample for immunological detection.

Finally, the invention relates to the use of the system as defined above to prepare a biological sample for detection by amplification.

BRIEF DESCRIPTION OF THE FIGURES

Other features and benefits will appear in the following detailed description in relation to the appended drawings in which.

DETAILED DESCRIPTION OF AT LEAST ONE EMBODIMENT

The process of the invention is intended for the preparation of a biological sample.

The biological sample is, for example, in the form of a fluid that contains biological species. The term 'biological species' is intended to mean microorganisms, cells, spores, toxins, etc. By way of example, a biological species may include a membrane and intracellular material such as nucleic acid (RNA, DNA) molecules from a cell, proteins, lipopolysaccharides (LPS), lipoteichoic acids (LTA), etc.

The term 'fluid' is intended to mean a liquid, a gas, etc. The liquid may have different degrees of viscosity and may for example be in the form of a paste or a gel.

In particular, the process makes it possible to prepare a sample for immunological detection and potentially also for an amplification reaction, using the same preparation device and the same starting sample.

According to a particular aspect of the invention, the device used is as described in patent application EP3222989A1.

Figure 1A:
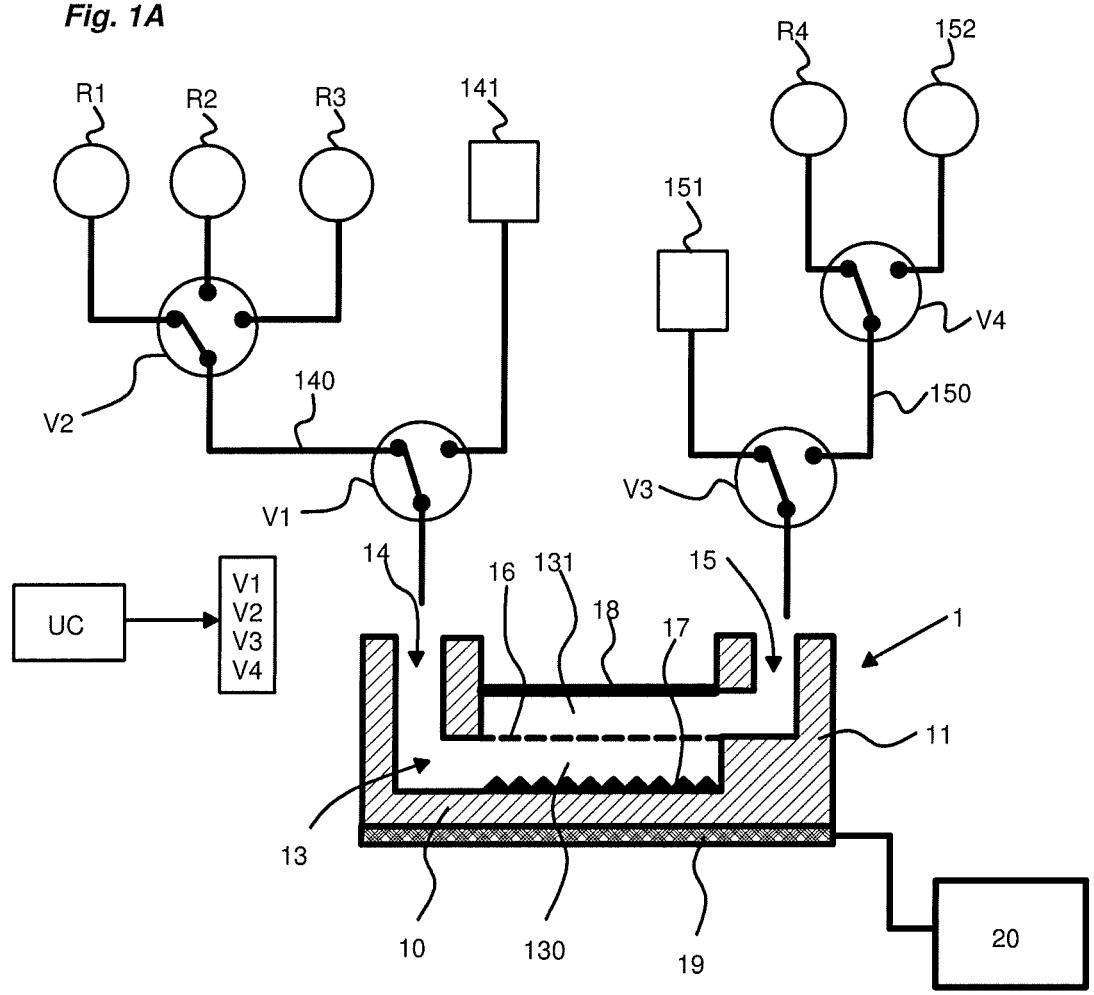
FIG. 1A shows an example of a preparation system used to implement the preparation process of the invention.
Figure 1B:
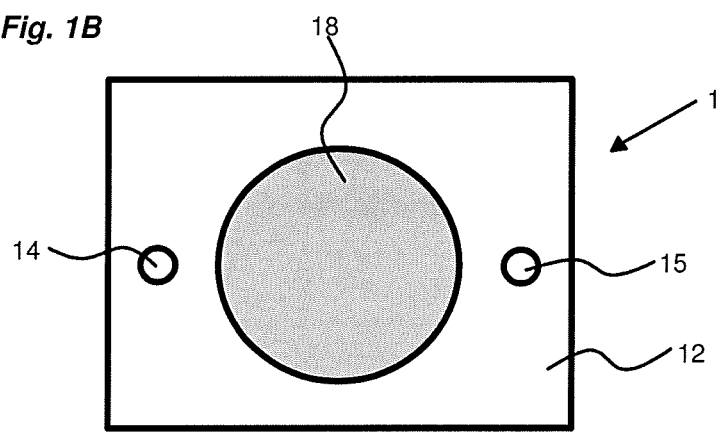
FIG. 1B is a top view of the preparation device used in the system in FIG. 1A.

The preparation device can be integrated into a more complete preparation system such as the one shown in FIG. 1A.

The preparation device 1 has a housing with a lower wall 10, a side wall 11 and an upper wall 12. All walls of the housing will preferentially be made of the same material. In particular, this material will be suitable for heating in a temperature range between 20° C. and 100° C. Preferentially, some walls of the housing, at least its side wall 11, will be made of a transparent material. Preferentially, the material used will be a plastic, for example poly(methyl methacrylate) (PMMA).

The device 1 has a chamber 13 provided in the housing. This chamber represents the location where purification/concentration, mechanical lysis, separation and potentially detection in biological species are carried out at the same time. The chamber 13 is closed towards the bottom by the lower wall of the housing.

The device has a first channel 14 to inject fluids into the chamber or to discharge fluids outside the chamber. The first channel 14 has a first end with an opening provided for example through the upper wall 12 of the housing and a second end that opens into said chamber 13. The first end of the first channel 14 is for example arranged vertically and its second end opens for example horizontally into the chamber 13. The first end of the first channel is for example widened out to accommodate a pipette tip or will be adapted to the type of device used to inject the fluid into the device. By way of example, it may be an opening which has a Luer-lock adapter for connecting a syringe or which is adapted to connect a fluid circuit such as the one described below.

The device has a second channel 15. This second channel 15 also has a first end that communicates with the exterior, forming an opening made for example through the upper wall of the housing and a second end that communicates with the space formed by the chamber 13. Via this second channel 15, it is also possible to inject fluids into said chamber or to discharge fluids outside said chamber. Its first end is for example arranged vertically and its second end horizontally. The chamber 13 is placed between the first channel 14 and the second channel 15. In the same way, the first end of this second channel is for example widened out to accommodate a pipette tip or will be adapted to the type of device used to inject the fluid into the device. By way of example, it may be an opening which has a Luer-lock adapter for connecting a syringe or which is adapted to connect a fluid circuit such as the one described below.

Towards the top, the chamber 13 can be closed with a flexible and stretchable, preferentially transparent, membrane 18. The upper wall 12 of the device housing thus has an opening that is sealed by said membrane 18. Said membrane is this anchored in the housing by any suitable fastening solution, for example by adhesive bonding. This membrane 18 will for example consist of a film, for example MicroAmp, 3M (registered trademarks), of suitable thickness, size and composition to deform elastically, relative to its anchoring points, in particular to the bottom of the chamber 13.

The term 'transparent' is intended to mean that the material used is at least partially transparent to visible light, so as to allow at least 80% of this light to pass through. This means that it will be transparent enough to see the interior of the chamber 13, at least the second space located above the filter.

The device includes a filter 16 arranged in said chamber 13 and separating said chamber 13 into two spaces. The two spaces are for example superimposed and thus denoted lower space 130 located under the filter and upper space 131 located above the filter. This filter 16 is preferentially made in whole or in part in the form of a thin flexible film, pulled in the space formed by the chamber so as to allow passage from one space to the other only via the pores of the filter 16. The film has an elastic deformability allowing it to stretch when exerting a bearing force in a substantially vertical direction, this elastic deformability having a sufficient level to reach the lower surface of the chamber 13. The filter 16 has an average pore diameter between 0.2 μm and 50 μm, for example between 0.2 μm and 1 μm, for the separation of microorganisms. The pore diameter is of course adapted to ensure separation between different biological species present in the sample. It will be seen that, after a step of lysis and of separation by the filter 16, the intracellular material (for example DNA molecules) can pass by elution above the filter 16, in the upper space 131 of the chamber, while the membranes remain below the filter, in the lower space 130 of the chamber. The filter 16 will be composed, for example, of a film of suitable thickness, size and composition to deform to the bottom of the chamber 13 relative to its anchoring points. According to a particular embodiment, the filter can also be made of a transparent material, for example with the same transparency characteristics as the membrane. For bacteria, the filter can have a pore diameter of 0.2 to 2 μm to retain the bacteria. After lysis, the DNA can be eluted through the filter.

The device can advantageously have a rough bearing surface 17 arranged on the bottom of the chamber 13. This rough bearing surface 17 extends over a majority of the bottom of the chamber. It has an average surface roughness parameter between 0.1 μm and 10 μm, preferentially between 0.2 μm and 3 μm. This rough bearing surface 17 is intended to allow mechanical lysis of the biological species present in a biological sample placed in the device. Preferentially, mechanical lysis is achieved by grinding said biological species by abrasion on said rough bearing surface. The grinding operation is carried out by a friction movement of the biological species against the rough bearing surface, using a suitable grinding member. This member will be, for example, a spatula 2 (see FIG. 2B) or a rod, for example made of plastic or metal. This member is applied from the exterior of the chamber 13 and its end is applied against the external surface of the membrane 18 so as to stretch the membrane 18 and the filter towards the bottom of the chamber and thus rub the biological species present in a sample against the rough bearing surface.

Preferentially, the housing can advantageously integrate means for heating the internal space of the chamber, composed for example of at least one heating element, as shown in the appended figures. The element is for example attached under the lower wall of the housing. A power source 20 will for example be provided to power the element 19. The power source will include, for example, one or more electric batteries, providing sufficient energy to heat the chamber to a temperature within the range defined above, i.e. 20° C. to 100° C. Of course, other heating means could be used, such as a conductive ink deposited by printing or screen printing under the lower wall of the housing.

Thus, to summarise, the device can advantageously include the following 'multilayer' structure:
- A lower rough bearing surface 17,
- A lower space 130 of the chamber 13 located above the rough bearing surface 17,
- A flexible and stretchable filter 16 located above the lower space 130,
- An upper space 131 of the chamber 13 located above the filter 16,
- A flexible and stretchable membrane 18 located above the upper space 131, sealing the chamber and accessible from the exterior of the device.

Furthermore, the preparation system, integrating said device, may advantageously include a controlled fluid circuit, cooperating with said device to carry out the process.

The fluid circuit advantageously includes several control valves allowing the implementation of the different steps of the process of the invention. The valves can be of any type, for example solenoid valves or other technical solution.

The circuit may include a first valve to connect the first end of the first channel 14 to an injection channel 140 or to an immunological detection device 141 that includes an immunological detection strip.

The first valve V1 can take one of the following two distinct states:
- The state S1 to connect only the first channel 14 to the injection channel 140;
- The state S2 to connect only the first channel 14 to the immunological detection device 141;
- The state S3 closed to isolate the chamber 13 from the exterior;

The injection channel 140 can be connected to three separate tanks R1, R2, R3, a first tank R1 containing the biological sample, a second tank R2 containing a wash buffer TP_L and a third tank R3 containing an amplification buffer TP_AMP, such as a reagent necessary for carrying out a polymerase chain reaction (PCR). A second four-way valve V2 can be interposed to select the tank to be connected to the injection channel 140.

The second valve V2 can take one of the following three distinct states:
- The state S1 to connect only the sample tank R1 to the injection channel 140;
- The state S2 to connect only the tank R2 of wash buffer TP_L to the injection channel 140;
- The state S3 to connect only the tank R3 of amplification buffer TP_AMP to the injection channel 140;

the system may include a third valve V3 to connect the first end of the second channel 15 to an amplification detection device 151 or to a third channel 150.

The third valve V3 can take one of the following two states:
- The state S1 to connect the second channel 15 only to the amplification detection device 151;
- The state S2 to connect the second channel 15 to the third channel 150;
- The state S3 closed to isolate the chamber 13 from the exterior;

the system may include a fourth valve V4 to connect this third channel 150 to a tank R4 to contain an immunoassay buffer TP_IM or to a waste bin 152.

The fourth valve V4 can take one of the following two states:
- The state S1 to connect the third channel 150 to the tank R4 of immunoassay buffer TP_IM;
- The state S2 to connect the third channel to the waste bin 152;

The different tanks can be of any type. One example is a syringe connected directly to the device 1 by suitable connectors. Another example is fluid capsules that can be activated by pressure (mechanical or pneumatic). The capsules can be made directly on a microfluidic chip.

The device 1 and the fluid circuit can be made on the same microfluidic chip, for example made of PMMA, with several layers to make the different elements of the system.

Such a system is therefore suitable for preparing a biological sample for several types of detection, particularly immunological detection and amplification reaction (for example PCR).

The system may include a processing and control unit UC to execute a control sequence adapted to the process to be implemented. The processing and control unit UC can in particular send control commands to switch each system valve from one state to another and/or to send control commands to each tank to control fluid injection into the system, following the steps of the process.

FIGS. 2A to 2E illustrate the implementation of the process of the invention and the different steps of sample preparation. Some steps are optional and can be omitted depending on the objective. The processing and control unit UC can send control commands to the system valves. In these figures, the arrows indicate the direction of flow of the fluid in the system.

Figure 2A:
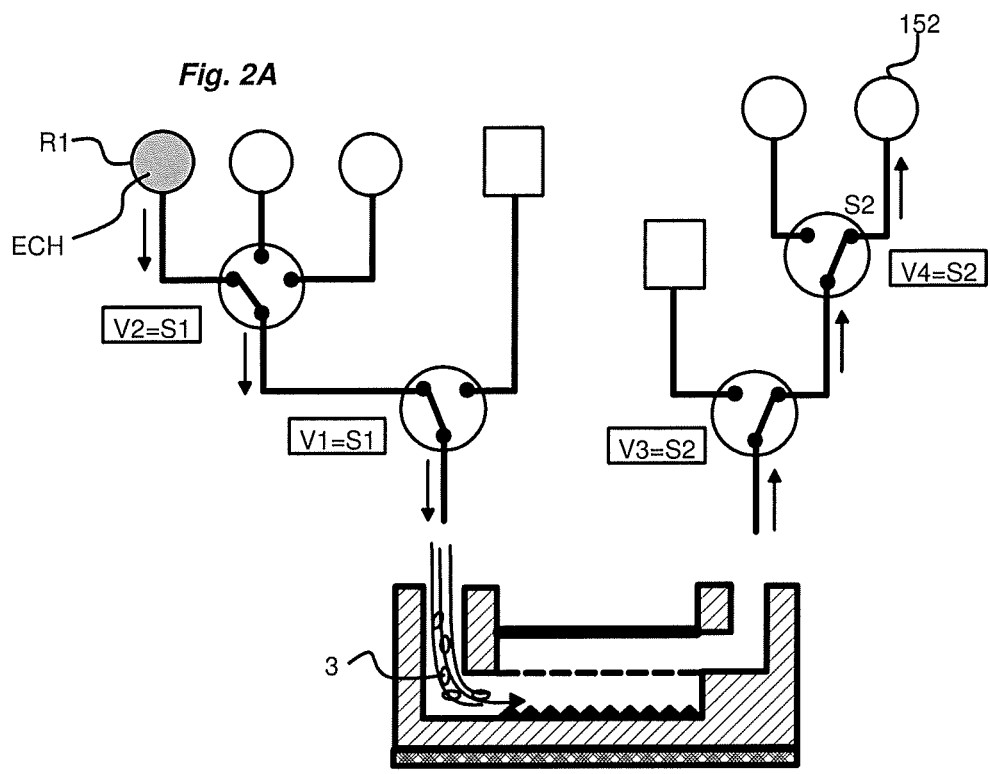
FIGS. 2A to 2F illustrate the different steps of the process of the invention, implemented using the system in FIG. 1A.

Step E1—FIG. 2A
Valve states:
V1=S1
V2=S1
V3=S2
V4=S2

The sample ECH in the tank R1 is injected in the form of a fluid via the first channel 14 into the chamber 13 of the device 1.

The portion of the sample not retained by the filter 16 in the lower space 130 of the chamber, passes through the filter 16 and is discharged to the waste bin 152 via the second channel 15 of the device.

The targeted biological species 3 remain trapped in the lower space 130 of the chamber 13.

Figure 2B:
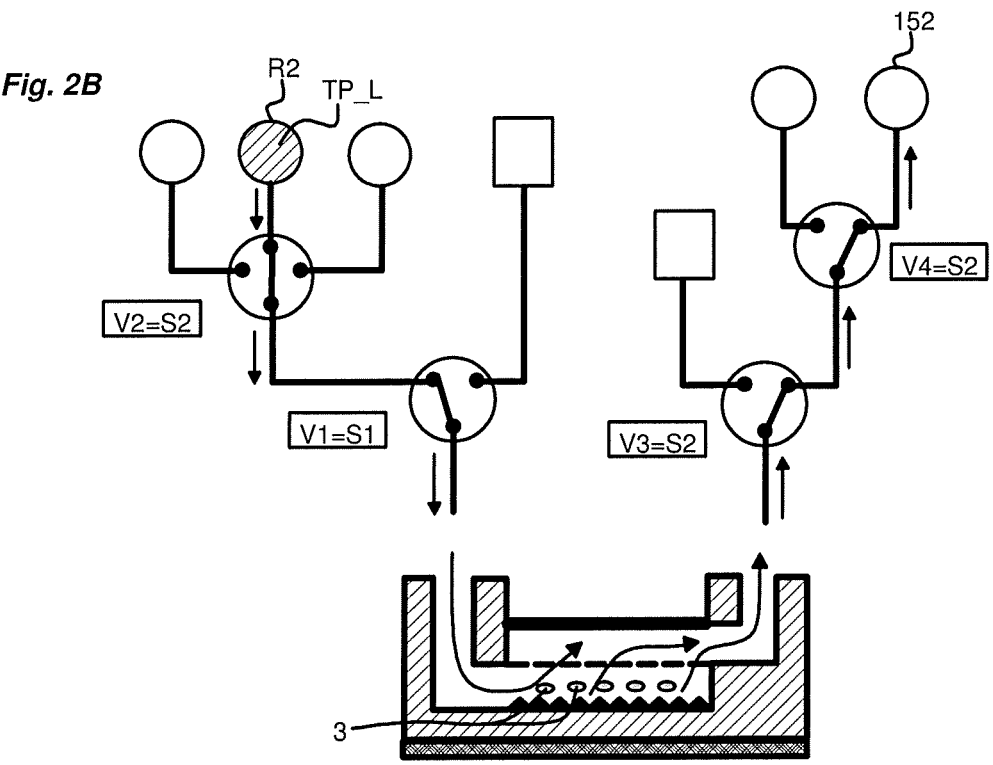

Step E2 (Optional)—FIG. 2B
Valve states:
V1=S1
V2=S2
V3=S2
V4=S2

This optional step purifies the biological species 3 already present in the lower space 130 of the chamber. The wash buffer TP_L in the tank R2 is injected into the first channel 14 and then discharged from the device via the second channel 15 to the waste bin 152.

Figure 2C:
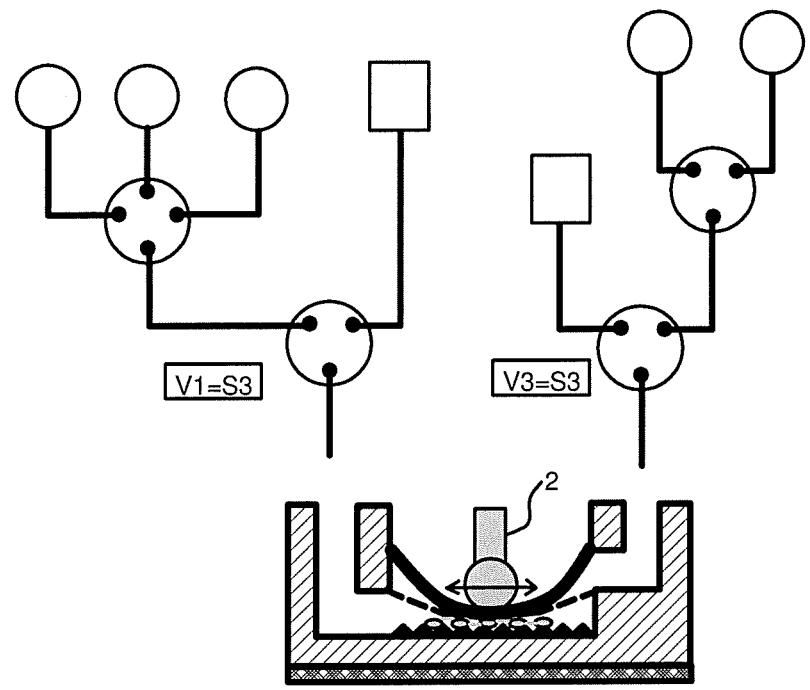

Step E3 (Optional)—FIG. 2C
  Valve states:
    V1=S3
    V3=S3

In this step, the first channel 14 and the second channel 15 of the device can be completely closed by closing the valves V1 and V3 to isolate the chamber 13 from the exterior.

The biological species 3 of the sample are lysed by grinding against the rough bearing surface 17 located at the bottom of the device 1.

Lysis generates a lysate comprising both intracellular material 30 and membranes 31.

This step is optional.

Figure 2D:
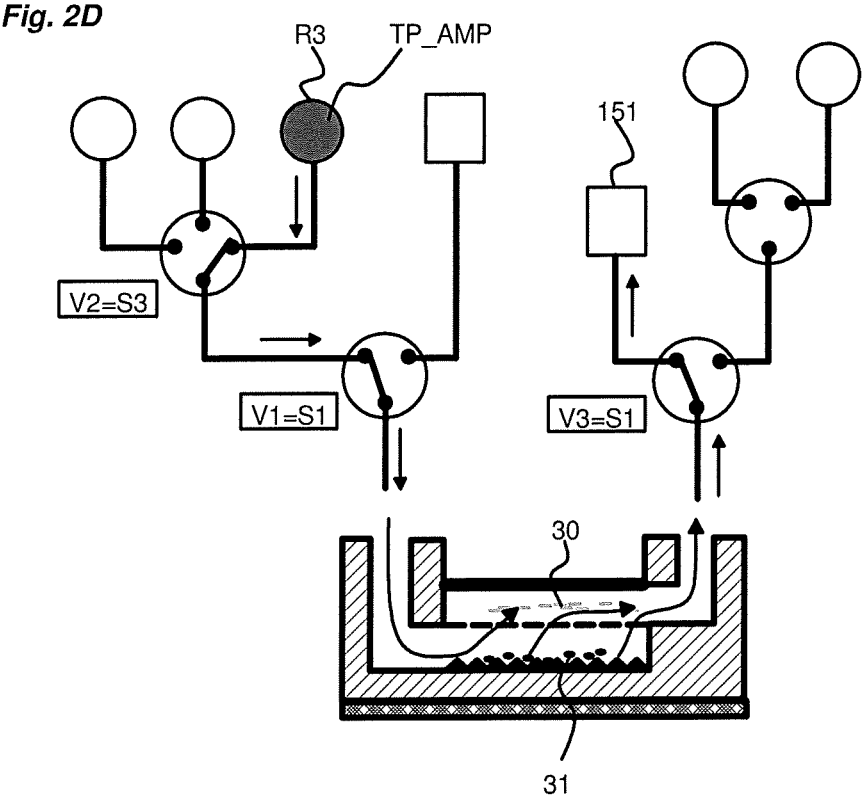

Step E4 (Optional)—FIG. 2D
  Valve states:
    V1=S1
    V2=S3
    V3=S1

This step makes it possible to elute the intracellular material obtained after lysis of the biological species and present in the lower space 130 of the chamber 13 to convey them to an amplification detection device. An amplification buffer TP_AMP comprising for example a PCR reagent, present in the tank R3, is injected via the first channel 14. The intracellular material 30 is eluted through the filter while the membranes 31 remain trapped in the lower space 130 of the chamber. The intracellular material 30 is eluted via the second channel 15 to an amplification detection device 151, for example to undergo PCR amplification.

This step is optional.

Figure 2E:
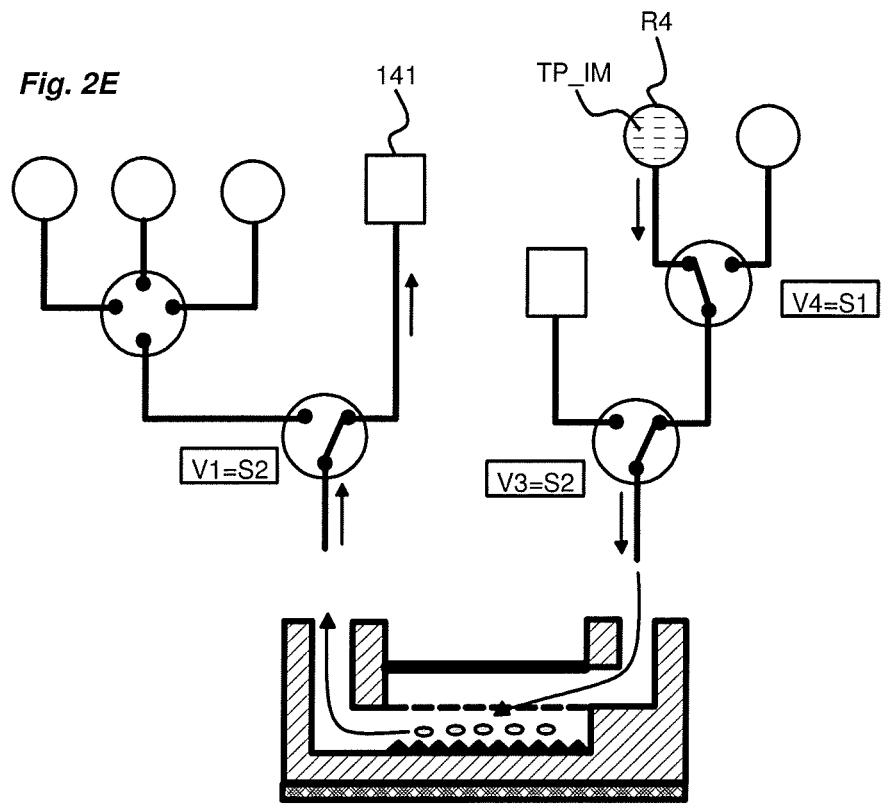
Figure 2F:
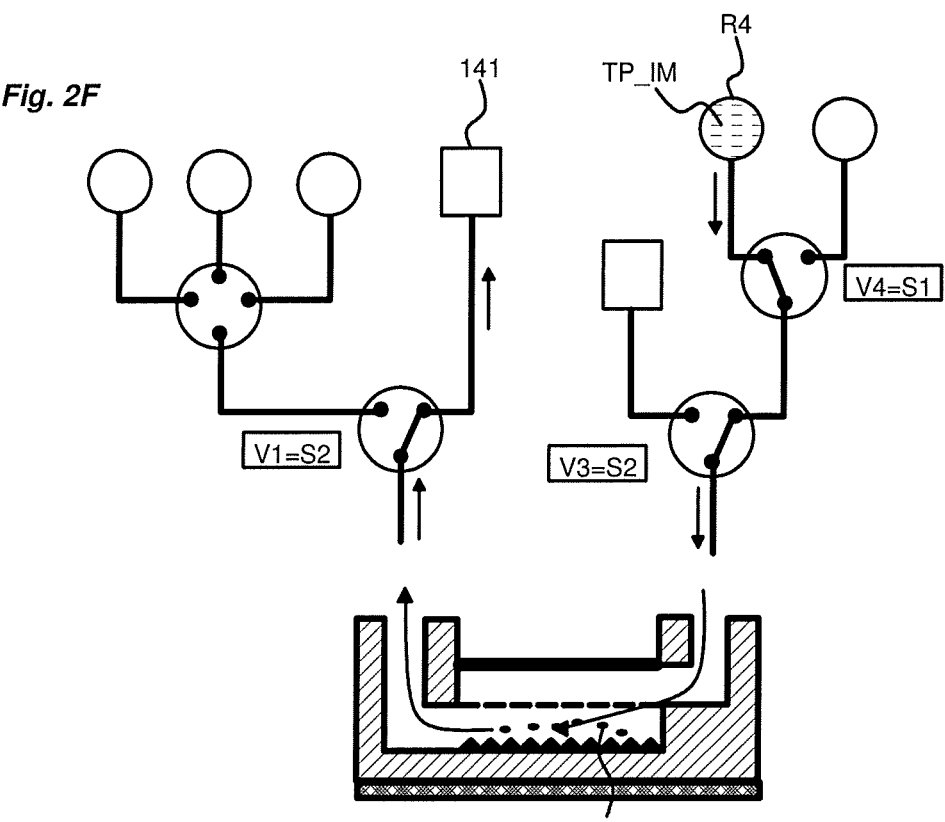

Step E5—FIGS. 2E and 2F
  Valve states:
    V1=S2
    V3=S2
    V4=S1

This step is carried out by injecting a fluid in the opposite direction to the previous one. An immunological buffer fluid TP_IM present in the tank R4 is injected via the second channel 15 allowing elution of biological species to the immunological detection device 141.

In this step, depending on whether or not the above-mentioned step E3 is performed, the biological species eluted to the immunological detection device are either the membranes 31 of the biological species (FIG. 2F—obtained after the lysis of step E3) or the biological species 3 of interest obtained from the beginning immediately after concentration performed in step El (FIG. 2E).

Advantageously, it will also be possible to provide a step of drying the filter 16 after each filtering or passage of a fluid through it. This drying step can be carried out by passing an air flow through the filter 16. The air flow can be created between the two channels 15, 16, for example by suction. The air flow can be created in either direction between the two channels.

Without limitation, the device may have the following size features:
  A first channel 14 composed of an inlet channel of 1 mm diameter×3 mm height, then a rectangular cross-section channel of 1 mm×150 μm of 3 mm length;
  A chamber 13 composed of a lower space 130 for concentration/lysis which has a diameter of 8 mm×150 μm in height and an upper space for elution of a diameter 8 mm×300 μm in height;
  The filter 16 with a porosity of 0.6 μm or 0.8 μm or porosity suitable for the target to be retained (virus, yeast, mould, etc.);
  A second channel 15 composed of a rectangular cross-section channel of 1 mm×150 μm and 3 mm long, then a channel of 1 mm diameter×3 mm height;

The preparation process of the invention, whether for immunological detection and/or for amplification detection, has the advantages defined below.

Performance provided by the preparation process of the invention, prior to detection by amplification:
  No loss of bacteria (during the concentration and purification step, losses of less than $1/10^8$ were observed);
  Improved lysis yield (e.g. on *B. anthracis*: only 1 in $10^6$ bacteria were not lysed);
  100% of the theoretical DNA found in amplification;
  Performance provided by the preparation process prior to immunological detection:
  Elimination of interference of immunological detection (acid, base, salts, etc.);
  Gain of a logarithm if concentration of a logarithm;
  Possible lysis which also allows intracellular membrane markers to be reached;
  Reduced risk for the operator when testing pathogenic bacteria; Only 1 in $10^6$ bacteria remains not lysed.

In addition, the following advantages are also observed:
Very simple sample preparation;
Very fast sample preparation, which can be carried out in less than 10 minutes;
A solution that does not divide the sample: no splitting to make two independent preparations, in particular to reduce the risks for the operator;
Each prepared sample comes out directly in its analytical reagent (no dilution or splitting of the sample for analysis). All targets present in the sample are engaged in the detection reaction (no dilution, no use of part of the eluate, etc.);
A sample preparation that allows both concentration and purification;
A lysis of very high efficiency. For example: Lysis of 100% of spores (species considered difficult to lyse). Membrane lysate deposited on a strip or ELISA;
A sensitivity comparable or even superior to the reference methods.

The invention claimed is:

1. A process for preparing a biological sample comprising biological species, implemented in a preparation system,
  wherein the preparation system comprises a device comprising:
    a housing comprising at least one opening,
    a first channel provided in the housing,
    a second channel provided in the housing,
    a chamber into which the first channel and the second channel lead, wherein the chamber comprises a rough bearing surface arranged on the bottom of the chamber which extends over a majority of the bottom of the chamber,
    a filter separating the chamber into two distinct spaces, wherein the first injection channel leads to a first space and the second channel leads to a second space, wherein the first space and the second space are partially superimposed such that the first space is a lower space in the chamber and is located under the filter and the second space is an upper space in the chamber and is located above the filter, such that the first space and the second space are in contact with each other in an superimposed area via the filter separating the first space and the and second space, wherein the filter has a porosity suitable for retaining the biological material to be analyzed, the process comprising:

injecting the biological sample in the form of a fluid via the first channel to concentrate biological species in the first space of the chamber of the device, conducting mechanical lysis of the biological species in the chamber by grinding the biological species by abrasion on the rough bearing surface, and separating cell membranes from an intracellular material, eluting the intracellular material by injecting an amplification buffer through the first channel of the device, to elute the material via the second channel, injecting an immunological buffer fluid via the second channel of the device and at least partially eluting the biological species with the immunological buffer fluid.

2. The process according to claim 1, further comprising carrying out washing after concentration by injecting a wash buffer via the first channel of the device, thereby purifying the biological species.

3. A system for preparing a biological sample that comprises biological species, wherein the system comprises a device that comprises:

a housing comprising at least one opening,
a first channel provided in the housing,
a second channel provided in the housing,
a chamber into which the first channel and the second channel lead,
a filter separating the chamber into two distinct spaces, wherein the first injection channel leads to a first space and the second channel leads to a second space, wherein the first space and the second space are partially superimposed such that the first space is a lower space in the chamber and is located under the filter and the second space is an upper space in the chamber and is located above the filter, such that the first space and the second space are in contact with each other in an superimposed area via the filter separating the first space and the and second space, wherein the filter has a porosity suitable for retaining the biological material to be analyzed, wherein the system comprises a fluid circuit connected to the device, wherein the fluid circuit comprises a plurality of controlled valves and a processing control unit configured to control the state of each valve to control the direction and flow of fluid within the system.

4. The system according to claim 3, wherein the fluid circuit comprises a first valve arranged to connect a first end of the first channel of the device to an injection channel or to an immunological detection device.

5. The system according to claim 4, wherein the fluid circuit comprises a second valve and three tanks and wherein the second valve is arranged to connect the injection channel to one of the three tanks.

6. The system according to claim 3, wherein the fluid circuit comprises a third valve arranged to connect a first end of the second channel to an amplification detection device or to a third channel.

7. The system according to claim 6, wherein the fluid circuit comprises a fourth valve arranged to connect the third channel to a tank to contain an immunoassay buffer or to a waste bin.

8. The system according to claim 3, which is a system for the preparation of a biological sample for immunological detection.

9. The system according to claim 3, which is a system for the preparation of a biological sample for detection by amplification.

10. The process according to claim 1, wherein the grinding is carried out by a friction movement of the biological species against the rough bearing surface using a grinding member.

11. The process according to claim 10, wherein the grinding member is a spatula or a rod, wherein the grinding member is applied from the exterior of the chamber and its end is applied against an external surface of a membrane to stretch the membrane and the filter towards the bottom of the chamber and to rub the biological species present in a sample against the rough bearing surface, and wherein the membrane is located towards the top of the chamber above the second space, and wherein an upper wall of the housing has an opening sealed by the membrane such that the membrane is anchored in the housing.

12. The process according to claim 1, wherein the housing comprises a membrane located towards the top of the chamber and above the second space, wherein an upper wall of the housing has an opening sealed by the membrane such that the membrane is anchored in the housing.

13. The process according to claim 1, wherein the rough bearing surface arranged on the bottom of the chamber has an average surface roughness parameter of from 0.1 μm to 10 μm.

14. The process according to claim 13, wherein the average surface roughness parameter of the rough bearing surface is from 0.2 μm and 3 μm.

* * * * *